United States Patent [19]

Eilingsfeld et al.

[11] 4,042,604

[45] Aug. 16, 1977

[54] ISOLATION OF DINITROANTHRAQUINONE HAVING A HIGH CONTENT OF $\alpha,\alpha$-DINITRO COMPOUNDS

[75] Inventors: Heinz Eilingsfeld, Frankenthal; Dietrich Lach, Ludwigshafen, both of Germany

[73] Assignee: BASF Aktiengesellschaft, Ludwigshafen (Rhine), Germany

[21] Appl. No.: 686,365

[22] Filed: May 14, 1976

[30] Foreign Application Priority Data

June 4, 1975  Germany .............................. 2524747

[51] Int. Cl.² .......................... C09B 1/00; C07C 79/37
[52] U.S. Cl. .................................................... 260/369
[58] Field of Search ......................................... 260/369

[56] References Cited

U.S. PATENT DOCUMENTS

| 1,622,168 | 3/1927 | Stein ....................................... 260/369 |
| 1,758,855 | 5/1930 | Schmidt et al. ........................ 260/369 |
| 3,929,841 | 12/1975 | Ackermann et al. ................. 260/369 |
| 3,939,185 | 2/1976 | Vogel ..................................... 260/369 |

*Primary Examiner*—Paul F. Shaver
*Attorney, Agent, or Firm*—Keil, Thompson & Shurtlefff

[57] ABSTRACT

A process for the isolation of mixtures of 1,5-dinitroanthraquinone and 1,8-dinitroanthraquinone which have a high content of $\alpha,\alpha'$-dinitroanthraquinones by heating a suspension of the crude dinitroanthraquinone mixture in certain organic liquids at from 60° to 200° C until solution equilibrium has been set up, and separating the undissolved material from the solution. The undissolved material contains more than 90% and as a rule more than 95% by weight of 1,5-dinitroanthraquinone and 1,8-dinitroanthraquinone. The pure mixture of 1,5-dinitroanthraquinone and 1,8-dinitroanthraquinone may be used for the manufacture of dyes.

8 Claims, No Drawings

ISOLATION OF DINITROANTHRAQUINONE HAVING A HIGH CONTENT OF α,α-DINITRO COMPOUNDS

The invention relates to a process for the isolation of mixtures of 1,5-dinitroanthraquinone and 1,8-dinitroanthraquinone having a high content of α,α'-dinitro compounds. The isolated product has a content of more than 90% and preferably of 95% by weight or more of 1,5-dinitroanthraquinone and 1,8-dinitroanthraquinone.

In the dinitration of anthraquinone there are formed not only the α,α'-dinitroanthraquinones but also a considerable amount of α,β'-dinitroanthraquinones and β,β'-dinitroanthraquinones. α,α'-dinitroanthraquinones are precursors for the production of valuable disperse dyes. The quality of some of these dyes is not affected when the dinitroanthraquinone mixture used as starting material contains large proportions of α,β'-isomers and β,β'-isomers. However, the quality of some particularly valuable dyes is decisively affected by the purity of the dinitroanthraquinone used as precursor. The content of α,β'-dinitro compounds and β,β'-dinitro compounds in the dinitroanthraquinone mixture is of great importance when the 1,5-dinitro and 1,8-dinitro compounds are to be separated by the method proposed in U.S. Pat. No. 3,929,841. A high quality 1,8-dinitroanthraquinone is only obtained from the filtrate when the mixture of 1,5-dinitroanthraquinone and 1,8-dinitroanthraquinone used as starting material is as pure as possible.

The object of the present invention is to provide a process in which there is obtained a high yield of a mixture of 1,5-dinitroanthraquinone and 1,8-dinitroanthraquinone which contains only a small proportion of the α,β'-isomers and β,β'-isomers from the mixture of crude dinitroanthraquinones obtainable by dinitration of anthraquinone.

This problem has hitherto been solved by nitrating the anthraquinone in concentrated sulfuric acid or in oleum so that the undesired α,β'-isomers and β,β'-isomers are kept in solution. The yield and purity of products obtained in this way are however unsatisfactory.

We have now found that a mixture of 1,5-dinitroanthraquinone and 1,8-dinitroanthraquinone having a high content of α,α'-isomers can be obtained from a mixture of crude dinitroanthraquinones by suspending the crude dinitroanthraquinone mixture in an organic liquid selected from chlorobenzene, notrobenzene, ethylbenzene, toluene, xylene, tetrahydronaphthalene, glycol monomethyl ether, glycol monoethyl ether, acetic acid, dichloroacetic acid, propionic acid and acetic anhydride, mixing (treating) the suspension at a temperature of from 60° to 200° C until solution equilibrium has been achieved and then separating the undissolved material from the suspension at the same temperature.

The said organic liquids dissolve the undesired α,β'-isomers and β,β'-isomers out from the crude dinitroanthraquinone mixture extensively to almost completely at elevated temperature whereas the desired α,α'-isomers have very little solubility under the treatment conditions. The residue obtained is a mixture of 1,5-dinitroanthraquinone and 1,8-dinitroanthraquinone which has a content of more than 90% by weight and as a rule of 95% or more by weight of the α,α'-isomers.

Of the solvents specified, xylene has proved to be particularly suitable, and for this reason purification is preferably carried out with this solvent. Pure isomers of xylene may be used or the commercial mixture of the isomers consisting of o-xylene, m-xylene and p-xylene is also suitable. A very pure mixture of 1,5-dinitroanthraquinone and 1,8-dinitroanthraquinone is obtained in a high yield with xylene. The use of xylene also has the advantage that crude dinitroanthraquinone which is moist may be used without impairing the results. Another advantage is that the solvent is easily recoverable by distillation. The residue obtained contains the extracted portion of the dinitroanthraquinone mixture which contains mainly 1,8-dinitroanthraquinone and the α',β-dinitro and β,β'-dinitro compounds. This mixture may if desired be used as a starting material for dyes.

The process according to the invention is generally carried out by suspending the dry or moist crude dinitroanthraquinone mixture in one of the abovementioned liquids, heating the suspension to a temperature of from 60° to 200° C, depending on the solvent used. When a moist dinitroanthraquinone mixture is used the water present is thus distilled off.

The suspension is stirred at the desired temperature until solution equilibrium has been achieved. As a rule this state is reached after from 30 minutes to six hours, depending on the solvent and the temperature to which it is heated. The undissolved material is then separated at the temperature at which the suspension was mixed to set up solution equilibrium, for example by filtration or centrifuging. The residue is advantageously washed with the same liquid.

All mixtures obtained according to prior art dinitration methods are suitable as crude dinitroanthraquinone mixtures for the process according to the invention. These mixtures usually contain from 65 to 80% by weight and in a few cases even up to 95% by weight of 1,5-dinitroanthraquinone and 1,8-dinitroanthraquinone. The remainder is α,β'-dinitroanthraquinone. For a given purification effect the yield is naturally better the higher the content of 1,5-dinitroanthraquinone and 1,8-dinitroanthraquinone in the crude dinitroanthraquinone mixture.

The amount of organic liquid depends mainly on the solubility of the α,β'-dinitroanthraquinone and β,β'-dinitroanthraquinone therein, on the content of α,α'-isomers in the crude dinitroanthraquinone mixture and on the temperature at which the treatment with the liquid is to be carried out.

As a rule the weight of organic liquid used is from one to thirty times the dry weight of the crude dinitroanthraquinone mixture. In the case of xylene the weight used is as a rule from twice to twenty times the weight of the crude dinitroanthraquinone mixture, depending on the purity thereof. An α,α'-dinitroanthraquinone mixture is then obtained with a content of about 98% of 1,5-dinitroanthraquinone and 1,8-dinitroanthraquinone.

The temperature also has an effect on the purity of the product because the undesired isomers dissolve better in the said liquids at higher temperature. Temperatures of from 60° to 200° C are generally used depending on the liquid used. When atmospheric pressure is used it is preferred to use a temperature range of from 30° C below the boiling temperature to the boiling temperature of the liquid or mixture of liquids used because optimal separation is achieved in this temperature range. In the case of xylene it is therefore advantageous to use temperatures of from 110° C to the boiling point (138° to 144° C depending on the content of the various isomers). When superatmospheric pressure is used it is possible to use temperatures which are above the boiling point at atmospheric pressure.

In order that solution equilibrium may be set up at the temperature, the suspension is stirred for another half an hour to six hours after the desired temperature has been reached. An α,α'-dinitroanthraquinone mixture of optimal purity is thus obtained. There is no advantage in stirring for a period longer than is necessary to set up solution equilibrium because no additional purification effect is achieved.

The following Examples will further illustrate the process according to the invention. Parts and percentages are by weight.

EXAMPLE 1

357 parts of a moist crude dinitroanthraquinone mixture (solids content 42% corresponding to 150 parts; content of 1,5-dinitroanthraquinone and 1,8-dinitroanthraquinone 80.4%) is heated with 1300 parts of a commercial xylene mixture (boiling point 138° C) and the water present removed azeotropically. After the water has been removed the temperature within the suspension rises to 138° C. The whole is stirred for another hour at 138° C and the hot suspension is suction filtered. The filtered material is washed with 130 parts of xylene and dried. The yield is 116 parts of a dinitroanthraquinone mixture with an overall content of 98.1% of 1,5-dinitroanthraquinone and 1,8-dinitroanthraquinone (=94.4% of the amount of α,α'-dinitroanthraquinone used with the crude dinitroanthraquinone mixture).

To determine the content of isomers in the dinitroanthraquinone mixture a sample in aqueous suspension is reduced with sodium sulfide at elevated temperature. The reduction takes place almost quantitatively. The diaminoanthraquinone mixture obtained is separated by column chromatography and the amount of individual amines determined spectrometrically. From the amounts determined the proportion of the individual isomers in the dinitroanthraquinone mixture can be calculated in relation to the weight of the sample.

EXAMPLES 2 TO 5

The procedure described in Example 1 is followed but the amounts of xylene set out in the Table are used instead of 1300 parts. The yields of 1,5-dinitroanthraquinone and 1,8-dinitroanthraquinone and the contents of 1,5-dinitroanthraquinone and 1,8-dinitroanthraquinone in the product are given in the Table. The columns in the Table are as follows:

A = Example No.
B = amount of xylene in parts
C = yield in parts of 1,5-dinitroanthraquinone and 1,8-dinitroanthraquinone
D = percentage content of 1,5-dinitroanthraquinone and 1,8-dinitroanthraquinone in the product C
E = percentage yield of 1,5-dinitroanthraquinone and 1,8-dinitroanthraquinone based on the 1,5-dinitroanthraquinone and 1,8-dinitroanthraquinone in the crude dinitroanthraquinone mixture.

Table

| A | B | C | D | E |
|---|---|---|---|---|
| 2 | 522 | 127 | 93.7 | 98.7 |
| 3 | 920 | 125 | 94.8 | 98.3 |
| 4 | 1044 | 120 | 96.8 | 96.3 |
| 5 | 1218 | 118 | 97.6 | 95.5 |

EXAMPLE 6

150 parts of dried dinitroanthraquinone mixture having a content of 91.3% of 1,5-dinitroanthraquinone and 1,8-dinitroanthraquinone is stirred with 780 parts of xylene for four hours at 138° C and then suction filtered while hot. The product is washed with 150 parts of xylene and 200 parts of methanol. The yield is 130 parts of a dinitroanthraquinone mixture containing 98% of 1,5-dinitroanthraquinone and 1,8-dinitroanthraquinone (corresponding to 95% of the 1,5-dinitroanthraquinone and 1,8-dinitroanthraquinone introduced into the purification).

EXAMPLE 7

50 parts of the (dried) dinitroanthraquinone mixture from Example 1 and 160 parts of dichloroacetic acid are stirred for 30 minutes at 170° C, then cooled to 100° C and suction filtered. The residue is washed with 80 parts of dichloroacetic acid and then with water. The yield is 34.8 parts of a dinitroanthraquinone mixture containing 97.2% of 1,5-dinitroanthraquinone and 1,8-dinitroanthraquinone (corresponding to 86.6% of the amount of 1,5-dinitroanthraquinone and 1,8-dinitroanthraquinone used for purification).

EXAMPLE 8

71.4 parts of moist dinitroanthraquinone mixture (solids content: 42%; amount of 1,5-dinitroanthraquinone and 1,8-dinitroanthraquinone; 80.9%) is slowly heated up to 140° C in 120 parts of nitrobenzene so that the water distils off. The whole is then stirred for one hour at 100° C and suction filtered at this temperature. The product is washed with 60 parts of nitrobenzene and 200 parts of methanol. The yield is 21 parts of dinitroanthraquinone mixture containing in all 98.1% of 1,5-dinitroanthraquinone and 1,8-dinitroanthraquinone (corresponding to 85.5% of the 1,5-dinitroanthraquinone and 1,8-dinitroanthraquinone in the dinitroanthraquinone mixture).

EXAMPLE 9

30 parts of a dry dinitroanthraquinone mixture which contains a total of 79.9% of 1,5-dinitroanthraquinone and 1,8-dinitroanthraquinone is heated with 279 parts of ethylene glycol monoethyl ether for three hours at 135° C. It is then suction filtered while hot. The residue is washed with 50 parts of ethylene glycol monoethyl ether and 100 parts of methanol. The yield is 20.2 parts of a mixture of 1,5-dinitroanthraquinone and 1,8-dinitroanthraquinone with a content of 97.8% of 1,5-dinitroanthraquinone and 1,8-dinitroanthraquinone (corresponding to 82.4% of the 1,5-dinitro and 1,8-dinitro compounds used in purification).

EXAMPLE 10

30 parts of the dinitroanthraquinone mixture specified in Example 9 is heated in 261 parts of xylene to 138° C. The whole is stirred for another six hours and then suction filtered while hot. The filter residue is washed with 50 parts of xylene and 100 parts of methanol. The yield is 23 parts of a product with a content of 98.1% of 1,5-dinitroanthraquinone and 1,8-dinitroanthraquinone (corresponding to 94.1% of the amount of 1,5-dinitroanthraquinone and 1,8-dinitroanthraquinone in the crude dinitroanthraquinone mixture).

The xylene in the mother liquor is recovered by steam distillation and the distillation residue is suction filtered and washed with water. The yield of residue is 6.8 parts.

EXAMPLE 11

50 parts of dry dinitroanthraquinone mixture which contains 65.2% of 1,5-dinitroanthraquinone and 1,8-dinitroanthraquinone is heated under reflux with 875 parts of xylene for three hours. The hot suspension is then suction filtered. The filtered material is washed with 130 parts of xylene and then dried. The yield is 30 parts of a mixture of 1,5-dinitroanthraquinone and 1,8-dinitroanthraquinone having a total content of 97.4% of 1,5-dinitroanthraquinone and 1,8-dinitroanthraquinone (corresponding to 89.6% of 1,5-dinitroanthraquinone and 1,8-dinitroanthraquinone introduced into the purification).

We claim:

1. A process for the isolation of a mixture of 1,5-dinitroanthraquinone and 1,8-dinitroanthraquinone having a high content of $\alpha,\alpha'$-isomers from a crude dinitroanthraquinone mixture which process comprises first suspending the crude dinitroanthraquinone mixture in from one to thirty times its own weight of xylene, heating the suspension to a temperature within the range of from 60° to 200° C mixing the suspension until solution equilibrium has been established, and then separating the undissolved material from the suspension at the same temperature used for said mixing.

2. A process as claimed in claim 1 wherein the amount of xylene used is from twice to twenty times the weight of the crude dinitroanthraquinone mixture.

3. A process as claimed in claim 1 wherein the suspension is heated to a temperature of from 30° C below the boiling point to the boiling point of the xylene, the solution equilibrium is set up and the undissolved material is separated at elevated temperature.

4. A process as claimed in claim 2 wherein the suspension is heated to a temperature within the range from 30° C below the boiling point to the boiling point of the xylene.

5. A process as claimed in claim 2 wherein the crude dinitroanthraquinone mixture is heated in xylene at a temperature of from 110° C to the boiling point to establish solution equilibrium.

6. A process as claimed in claim 1 wherein a moist crude dinitroanthraquinone mixture is used and the water is removed therefrom during the heating up.

7. A process as claimed in claim 2 wherein a moist crude dinitroanthraquinone mixture is used and the water is removed therefrom during heating up.

8. A process as claimed in claim 1 wherein the xylene used is a mixture of O-xylene, m-xylene and p-xylene.

* * * * *